(12) United States Patent
Uriarte et al.

(10) Patent No.: US 6,255,539 B1
(45) Date of Patent: Jul. 3, 2001

(54) CHEMICAL COMPOSITION AND PROCESS

(75) Inventors: Anthony K. Uriarte, Pensacola, FL (US); Christopher R. Buechler, Pensacola Beach, FL (US); Jerry R. Ebner, St. Peters, MO (US); Michael J. Gross, Cantonment, FL (US); William D. McGhee, St. Louis, MO (US); Jayne E. Morris, Cantonment, FL (US); Erik D. Sall, Chesterfield, MO (US)

(73) Assignee: Solutia Inc., St. Louis, MO (US)

( * ) Notice: Subject to any disclaimer, the term of this patent is extended or adjusted under 35 U.S.C. 154(b) by 0 days.

(21) Appl. No.: 08/942,955

(22) Filed: Oct. 2, 1997

Related U.S. Application Data
(60) Provisional application No. 60/027,553, filed on Oct. 7, 1996.

(51) Int. Cl.$^7$ .................................................. C07C 37/00
(52) U.S. Cl. ............................................................ 568/800
(58) Field of Search .................................. 568/629, 800, 568/767, 771, 763

(56) References Cited

U.S. PATENT DOCUMENTS

| | | | |
|---|---|---|---|
| 4,258,222 | 3/1981 | Möhring et al. | 568/863 |
| 4,982,013 | 1/1991 | Gubelmann et al. | 568/771 |
| 5,001,280 | 3/1991 | Gubelmann et al. | 568/716 |
| 5,019,657 | 5/1991 | Gubelmann et al. | 568/774 |
| 5,055,623 | 10/1991 | Gubelmann et al. | 568/800 |
| 5,110,995 | 5/1992 | Kharitonov et al. | 568/800 |
| 5,171,553 | 12/1992 | Li et al. | 423/239 |
| 5,502,259 | 3/1996 | Zakoshansky et al. | 568/754 |

FOREIGN PATENT DOCUMENTS

| | | |
|---|---|---|
| 0 406 050 A2 | 6/1990 | (EP) . |
| 2 116 974 | 3/1993 | (GB) . |
| 5-16179 | 2/1993 | (JP) . |
| 2 010 790 | 4/1994 | (RU) . |
| WO 95/27560 | 10/1995 | (WO) . |
| WO 95/27691 | 10/1995 | (WO) . |

OTHER PUBLICATIONS

Li et al. (1992) Catalytic Decomposition Of Nitrous Oxide On Metal Exchanged Zeolites, Applied Catalysis B: Environmental 1, L21–29, Elsevier Science Publishers B.V., Amsterdam.

Sobolev et al. (1993) Catalytic Properties Of ZSM–5 Zeolites in $N_2O$ Decomposition: The Role Of Iron; Journal of Catalysis 139, 435–443, Academic Press, Inc.

Sobolev et al. (1993) Stoichiometric Reaction Of Benzene With α–Form Of Oxygen On Fezsm–5 Zeolites. Mechanism Of Aromatics Hydroxylation By $N_2O$; Journal of Molecular Catalysis 84, 117–124; Elsevier Science Publishers B.V., Amsterdam.

Panov et al. (1992) Oxidation Of Benzene To Phenol By Nitrous Oxide Over Fe–ZSM–5 Zeolites; Applied Catalysis A: General 82, 31–36, Elsevier Science Publishers B.V., Amsterdam.

Kharitonov et al. (1993) Ferrisilicate Analogs Of ZSM–5 Zeolite As Catalysts For One Step Oxidation Of Benzene To Phenol; Applied Catalysis A: General 98, 33–43, Elsevier Science Publishers B.V., Amsterdam.

Burch et al. (1993) Factors Affecting The Deactivation Of Various Zeolites Used As Catalysts For The Direct Partial Oxidation Of Benzene To Phenol; Applied Catalysis A: General 106, 167–183, Elsevier Science Publishers B.V. , Amsterdam.

Burch et al. (1993) Investigation Of Zeolite Catalysts For The Direct Partial Oxidation Of Benzene To Phenol; Applied Catalysis A: General 103, 135–162, Elsevier Science Publishers B.V., Amsterdam.

Burch et al. (1993) Direct Partial Oxidation Of Benzene To Phenol On Zeolite Catalysts; Applied Catalysis A: General 86, 139–146, Elsevier Science Publishers B.V., Amsterdam.

Panov et al. (1993) Oxidative Hydroxylation Using Dinitrogen Monoxide: A Possible Route For Organic Synthesis Over Zeolites, Applied Catalysis A: General, 98, pp. 1–20, Elsevier Science Publishers B.V., Amsterdam.

Dvorak et al. (1970) Determination Of The Specific Copper Surface Area By Chromatographic Technique; Journal of Catalysis 18, 108–114, Academic Press, Inc.

Evans et al. (1983) On The Determination Of Copper Surface Area By Reaction With Nitrous Oxide; Applied Catalysis 7, 75–83, Elsevier Science Publishers B.V.

Iwamoto et al. (1983) Catalytic Oxidation By Oxide Radical Ions. 1. One–Step Hydroxylation Of Benzene To Phenol Over Group 5 And 6 Oxides Supported On Silica Gel; The Journal of Physical Chemistry 87, No. 6, The American Chemical Society.

Ono et al. (1988) Functionalization Of Benzene By Its Reaction With Nitrogen Oxides Over Solid–Acid Catalysts, Herterogeneous Catalysis and Fine Chemicals, pp. 75–82, Elsevier Science Publishers B.V. Amsterdam.

Suzuki et al. (1988) Hydroxylation Of Benzene With Dinotrogen Monoxide Over H–ZSM–5 Zeolite, Chemistry Letters, pp. 953–956, The Chemical Society of Japan.

Panov et al. (1990) The Role Of Iron In $N_2O$ Decomposition On ZSM–5 Zeolite And Reactivity Of The Surface Oxygen Formed, Journal of Molecular Catalysis 61, 85–97, Elsevier Sequoia.

(List continued on next page.)

Primary Examiner—Michael L. Shippen
(74) Attorney, Agent, or Firm—Arnold, White & Durkee

(57) ABSTRACT

Inert gas additive is utilized in the catalytic oxidation of benzene with nitrous oxide to produce phenol in order to prevent excessive exothermic temperature increases and to render gaseous mixtures throughout the process non-flammable.

11 Claims, No Drawings

OTHER PUBLICATIONS

Sobolev et al. (1991) Anomalously Low Bond Energy Of Surface Oxygen On FeZSM–5 Zeolite, Mendeleev Communications, No. 1, pp. 29–30.

Zholobenko (1993) Preparation Of Phenol Over Dehydroxylated NZSM–5 Zeolites, Mendeleev Communications, pp. 23–24.

Hafele et al. (1996) Hydroxylation of Benzene on ZSM5 Type Catalysts, DGMK–Conference, Catalysis On Solid Acids and Bases, pp. 243–251.

Vereshchagin et al., Conversion Of Ethane On Zeolite Catalysts In The Presence Of Oxygen And Nitrogen(I) Oxde., Izv. Akad. Nauk SSSR, Ser. Khim., (1988), (8), 1718–1722 (English abstract translated from Russian article).

Derwent abstract; JP 5 009 142.

Derwent abstract, JP 4 334 333.

Derwent abstract, JP 4 021 645.

Derwent abstract, JP 6 009 464.

Derwent abstract, JP 6 040 976.

CHEMICAL COMPOSITION AND PROCESS

This application claims benefit of U.S. provisional application No. 60/027,553, filed on Oct. 7, 1996, now abandoned.

BACKGROUND OF THE INVENTION

The production of phenol or phenol derivatives by catalytic partial oxidation of benzene or benzene derivatives is known. For example, the use of a variety of catalysts such as vanadium pentoxide on silica or zeolites (e.g. ZSM-5 and ZSM-11) at elevated temperatures has been disclosed in, for example, Iwamoto et al., J. Physical Chemistry (ACS), Vol. 87, No. 6, (1983) p. 903–905; Suzuki et al., 1988 Chemistry Letters of the Chemistry Society of Japan at pages 953–956; U.S. Pat. Nos. 5,001,280, 5,110,995, and 5,055,623, the disclosures of these publications being incorporated herein by reference.

Although useful for production of both phenol and phenol derivatives, the most significant potential utility of such processes is for the production of phenol in view of the commercial importance of that compound.

To date, practical commercial use of such processes has been hindered by low productivity, problems in controlling temperature rise of the highly exothermic reaction and resulting formation of undesired by-products, and the flammability of mixtures of nitrous oxide and benzene.

Recently processes of this type have been remarkably improved by the discovery that use of a molar deficiency of nitrous oxide (as opposed to the excess or at least stoichiometric quantities previously utilized) will increase selectivity to desired products, provide for higher conversion of nitrous oxide and higher catalyst production efficiency and can also allow for lower temperature rises resulting from the exothermic reaction and for operation with non-explosive mixtures. This discovery is described in detail in U.S. patent application Ser. No. 08/419371 filed Apr. 10, 1995 and copending herewith, the disclosure of said application being incorporated herein by reference.

However the use of large excesses of benzene beyond the amount required to optimize reaction selectivity requires the separation and recycle of large amounts of benzene. Even if benzene ratios are high enough to provide non-flammable mixtures in the reactor, the separation of benzene for recycle in downstream operations may leave flammable or explosive mixtures of benzene and nitrous oxide in downstream apparatus if nitrous oxide consumption in the reaction is less than 100%. Moreover, benzene is a flammable, toxic chemical and storage and handling of large excesses of that required for reaction increases the magnitude of potential leaks.

It is therefore recognized by those skilled in the art that techniques for limiting the excess of benzene to amounts dictated by productivity considerations and, simultaneously, achieving control of flammability and/or adiabatic temperature rise problems would represent a needed advance in the art.

SUMMARY OF THE INVENTION

The present invention provides mixtures for use in processes for production of phenol and phenol derivatives and processes utilizing mixtures of the type described. The mixtures are characterized by a nitrous oxide to benzene ratio less than 0.5 and sufficient inert gas to render the mixture non-flammable. The use of preferred proportions of nitrous oxide, benzene, and inert gas permits the reaction to be conducted adiabatically without excessive temperature rise.

The invention will be further understood from the description of the preferred embodiments.

DESCRIPTION OF THE PREFERRED EMBODIMENTS

The present invention constitutes mixtures for use in processes and processes for catalytic partial oxidation of benzene or substituted benzene by reaction with nitrous oxide in the presence of a catalyst to form phenol or substituted phenol. The mixture and process will be described by reference to the reaction of benzene to form phenol. It will be understood that the use of substituted benzenes instead of benzene will result in production of the corresponding substituted phenols.

In accordance with the process of the present invention, a mixture of benzene and nitrous oxide is contacted with a catalyst in a reactor under conditions selected to oxidize the benzene to phenol. The molar ratio of nitrous oxide to benzene in the mixture will be less than 0.5. Preferably, the ratio of nitrous oxide to benzene will be sufficiently low to provide at least 50 mole percent, most preferably 75 to 85 percent, of the obtainable selectivity of the reaction of benzene to phenol. By "obtainable selectivity" is meant the maximum selectivity of benzene to phenol which can be obtained for given reaction conditions and catalyst by reducing the mole ratio of nitrous oxide to benzene. It is noted that selectivity approaching 100 percent can be obtained but usually at the cost of lower productivity. When preferred catalysts are utilized at normal reaction temperatures, obtainable selectivity is typically approached or attained at a nitrous oxide to benzene ratio of about 0.1. Down-stream from the reactor, the unreacted benzene is separated from the product by conventional separation techniques and recycled to the reactor.

A critical requirement of the invention is that an inert gas (that is, a gas which will not adversely affect or undesirably participate in the reaction, or adversely affect the catalyst) be present throughout the process in an amount sufficient to render the various benzene/nitrous oxide mixes encountered throughout the process non-flammable. (Flammability/non-flammability is determined pursuant to ASTM Standard E918). For most catalysts and reaction conditions, nitrogen, carbon dioxide, helium, argon, or mixtures thereof will constitute a satisfactory inert gas. It will be understood that different proportions of inert gas may be required in different portions of the process to satisfy the minimum requirement. For example, the ratio of nitrous oxide to benzene in the reactor may be sufficiently low in the reactor to be non-flammable even in the absence of any inert gas. However downstream removal of benzene for recycle may leave residual flammable vapor mixes of nitrous oxide and benzene in separation apparatus or other portions of the system. Such a situation would require injection of inert gas prior to or in the separator. Preferably, from the standpoint of simplicity of process control, sufficient inert gas will be included in the reactor vessel mixture to assure that downstream mixes within expected nitrous oxide to benzene ranges will be non-flammable. The inert gas will remain admixed with nitrous oxide during separation of benzene and/or phenol and thus be available to make its anti-flame function available in any downstream nitrous oxide containing mixture.

Maximum protection against flammability can be provided by means of a mixture which has a sufficiently high ratio of inert gas to nitrous oxide that the mixture will be non-flammable regardless of the amount of benzene therein. This will be the case if the molar ratio of nitrous oxide to inert gas is 0.25 or less. Such a mixture may be safely stored as a premixed feed and its use will insure against problems resulting from unexpectedly low conversion of nitrous oxide or other reaction variation. Of course, preferred mixtures will also contain proportions of benzene and nitrous oxide optimized for selectivity of phenol product. Use of excess inert gas is, within practical limits, unobjectionable and provides added protection against leakage of oxidizer (air) into the system.

It is preferred that the mixture of nitrous oxide, benzene and inert gas used in the reactor contains at least 0.3 mole percent nitrous oxide but less than 5 mole percent, most preferably less than 3 mole percent. Lower amounts tend to restrict productivity and higher amounts make it more difficult to control flammability and adiabatic temperature rise.

By selecting the proportions of the mixture in the reactor adiabatic temperature rise from the exothermic reaction can be limited to 150 degrees C. or less. When this is done the reaction can be carried out adiabatically eliminating the use of costly heat exchange means without unduly increasing formation of undesired by-products. Increasing the inert gas or benzene content of the mixture for temperature control also renders the mixture less flammable.

It will be apparent from the foregoing discussion that the maximum advantages of the invention will be obtained in process where, absent the inert gas, flammable vapor mixtures would be encountered and/or adiabatic temperature rises greater than 150 degrees C. experienced. However, even in other systems the inert gas will provide insurance against reaction disturbances which might otherwise result in flammable mixtures or unacceptable temperature rises. For example, in a system in which nitrous oxide is initially 100% reacted the inert gas will protect against flammable mixture formation in the event nitrous oxide conversion drops due to catalyst deterioration or other cause.

The proportions of nitrous oxide, benzene and inert gas set forth above are based on the proportions of only these materials in the process system. It will be understood that the system will also contain phenol and usually small amounts of various by-products and/or co-products. Also minor amounts of various contaminants such as water vapor, oxygen, carbon monoxide, nitric oxide, nitrogen dioxide and various organics can be tolerated.

The process will generally be conducted in a temperature range of from 250–600 degrees C. Higher temperatures may result in formation of undesirably high levels of by-products whereas lower temperatures may unduly slow the rate of reaction with most catalysts. However, any temperature providing an acceptable reaction rate without excessive by-product formation may be utilized. Any catalyst effective for the partial oxidation of benzene or substituted benzene to phenol or substituted phenol may be utilized. For example, vanadium pentoxide on silica or various zeolites may be employed. Preferred catalysts include acidified ZSM-5 and ZSM-11 containing catalytically effective amounts of iron. Further, productivity of the process can be enhanced by using a zeolite that has been hydrothermally treated by exposure to water vapor in air at about 500–900 degrees C. for about 2 hours. Such treatment is described in U.S. patent application Ser. No. 08/419361 filed Apr. 10, 1995 and copending herewith, now abandoned the disclosure of said application being incorporated herein by reference.

In general, the process will be operated to maximize benzene selectivity for phenol (moles of phenol produced per mole of benzene reacted); to maximize nitrous oxide selectivity for phenol (moles of phenol produced per mole of nitrous oxide reacted); to maximize productivity (mass of phenol produced per unit time divided by catalyst mass); and to minimize catalyst activity loss rate.

The primary reaction to convert benzene to phenol is accompanied by various side reactions including: a reaction converting benzene to coke; a reaction converting benzene to carbon dioxide and carbon monoxide; and a reaction converting benzene to various partially oxygenated aromatics, e.g. dihydroxybenzenes. All of the reaction rates are increased by increasing temperature but the rate of the side reactions is increased more than the rate of the desired reaction producing the primary product. Also, the greater the rate of side reactions, the faster the rate of catalyst activity loss. Selectivity and yields are optimized by lowering temperature and/or nitrous oxide concentration.

In an adiabatic reactor, temperature can be lowered by lowering the temperature of feed streams to the reactor (reactants and diluents). However, lowering the feed stream temperature too much will adversely affect productivity. The optimum temperature for a given system can be determined by routine tests to give the desired balance between selectivity and productivity. Adiabatic temperature rise can be minimized by lowering nitrous oxide conversion (moles nitrous oxide reacted per mole nitrous oxide fed to the reactor); by increasing the heat capacity of the feed stream; or by the nitrous oxide concentration in the feed. Nitrous oxide concentration can be lowered two ways to favor the desired reaction. First, of course the mole percent nitrous oxide in the feed can simply be reduced taking care that the concentration is not reduced so much as to unduly affect productivity. The second method is to decrease the feed stream flow rate (resulting in increased contact time with the catalyst) so as to decrease the average concentration of nitrous oxide. Again, this cannot be overdone or productivity will suffer.

It will be recognized that the variables discussed above other than the proportions of feed components are not independent. For example, increasing the feed temperature increases the reactor exit temperature because it increases the reaction rate and nitrous oxide conversion. Also, the average nitrous oxide concentration in the reactor decreases due to higher conversion. The yield of nitrous oxide to phenol will depend on whether the benefit from the lower nitrous oxide concentration is greater or less than the penalty for the higher temperature. Similarly, the productivity will depend on whether any decrease in selectivity is offset by an increase in nitrous oxide conversion.

As has been indicated, benzene may be replaced in whole or part by substituted benzenes such as phenol, fluorobenzene, chlorobenzene, toluene, ethyl benzene and similar compounds having an aromatic ring with a substitutable hydrogen atom on the ring. The process is also useful to produce polyols such as hydroquinone, resorcinol, and catechol by oxidation of phenol. When only phenol is desired, further oxidation to polyols (aromatics having more than one —OH substituants) can be minimized by using a low feed ratio of nitrous oxide to benzene, a low temperature, and maximizing nitrous oxide conversion.

The invention is further illustrated by the following examples:

EXAMPLES 1–18

In the examples, a gas mixture containing the proportions of benzene, nitrous oxide, and nitrogen shown in the following table is fed to an adiabatic reactor having a fixed bed of ZSM-5 type zeolite catalyst having a silica to alumina molar ratio of 100 and containing 0.45 weight percent ferric oxide. Catalyst of this type can be made by procedures such as described by Ione et al. in Usp. Khimii, 1987, Vol. 56, No. 3, p. 393. The reactor exit gas will contain, in addition to phenol and unreacted feed stream components, small (<0.3% by weight) amounts of carbon dioxide, carbon monoxide, high boiling point organic impurities, water and oxygen. The exit gas mixture is passed through a condenser and vapor/liquid separator operated such that the temperature at the condenser exit is 15 degrees Centigrade and the pressure is 1 atm. The condensed liquid containing most of the phenol and benzene is processed to separate the benzene which is recycled to the reactor.

EXAMPLES 1–18

| # | Stream #1 = Feed Gas Composition (mole %) | | | N₂O to Phenol Molar Yield (%) in Reactor | Reactor Temperature Profile (degrees C.) | | | Stream #2 = Reactor Exit Gas Composition (mole %) ASSUMES NO BY-PRODUCTS FORMED, TO SIMPLIFY CALCULATIONS | | | | Stream #3 = Vent Gas Composition, from 15° C., 1 atm Condensation Step to Recover Benzene and Phenol (mole %) | | | Flammability of Gas Streams (F = flammable) (NF = non flammable) | | |
|---|---|---|---|---|---|---|---|---|---|---|---|---|---|---|---|---|---|
| EX | N₂O | C₆H₆ | N₂ | | Inlet | Exit | Rise | N₂O | C₆H₆ | N₂ | C₆H₅OH | N₂O | C₆H₆ | N₂ | #1 | #2 | #3 |
| 1 | 2 | 20 | 78 | 75 | 400 | 464 | 64 | 0.5 | 18.5 | 79.5 | 1.5 | 0.6 | 6.6 | 92.8 | NF | NF | NF |
| 2 | 4 | 20 | 76 | 75 | 400 | 525 | 125 | 1.0 | 17.0 | 79.0 | 3.0 | 1.2 | 6.1 | 92.7 | NF | NF | NF |
| 3 | 6 | 20 | 74 | (75) | 400 | 584 | 184 | 1.5 | 15.5 | 78.5 | 4.5 | 1.8 | 5.6 | 92.6 | NF | NF | NF |
| 4 | 8 | 20 | 72 | (75) | 400 | 640 | 240 | 2.0 | 14.0 | 78.0 | 6.0 | 2.4 | 5.3 | 92.4 | NF | NF | NF |
| 5 | 10 | 20 | 70 | (75) | 400 | 695 | 295 | 2.5 | 12.5 | 77.5 | 7.5 | 3.0 | 4.9 | 92.1 | NF | NF | NF |
| 6 | 5 | 50 | 45 | 75 | 400 | 492 | 92 | 1.3 | 46.2 | 48.7 | 3.8 | 2.3 | 6.7 | 91.0 | NF | NF | NF |
| 7 | 10 | 50 | 40 | (75) | 400 | 577 | 177 | 2.5 | 42.5 | 47.5 | 7.5 | 4.7 | 6.3 | 89.0 | NF | NF | NF |
| 8 | 15 | 50 | 35 | (75) | 400 | 656 | 256 | 3.8 | 38.7 | 46.2 | 11.3 | 7.0 | 5.9 | 87.1 | NF | NF | NF |
| 9 | 20 | 50 | 30 | (75) | 400 | 731 | 331 | 5.0 | 35.0 | 45.0 | 15.0 | 9.4 | 5.5 | 85.1 | NF | NF | NF |
| 10 | 25 | 50 | 25 | (75) | 400 | 804 | 404 | 6.3 | 31.3 | 43.7 | 18.7 | 11.8 | 5.2 | 83.0 | NF | NF | NF |
| 11 | 4 | 80 | 16 | 75 | 400 | 453 | 53 | 1.0 | 77.0 | 19.0 | 3.0 | 4.7 | 7.0 | 88.3 | NF | NF | NF |
| 12 | 8 | 80 | 12 | 75 | 400 | 503 | 103 | 2.0 | 74.0 | 18.0 | 6.0 | 9.3 | 6.7 | 84.0 | NF | NF | NF |
| 13 | 12 | 80 | 8 | 75 | 400 | 550 | 150 | 3.0 | 71.0 | 17.0 | 9.0 | 14.0 | 6.5 | 79.5 | NF | NF | NF |
| 14 | 16 | 80 | 4 | (75) | 400 | 596 | 196 | 4.0 | 68.0 | 16.0 | 12.0 | 18.7 | 6.3 | 75.0 | NF | NF | NF |
| 15 | 20 | 80 | 0 | (75) | 400 | 641 | 241 | 5.0 | 65.0 | 15.0 | 15.0 | 23.4 | 6.1 | 70.5 | NF | NF | NF |
| 16 | 10 | 40 | 50 | (75) | 400 | 603 | 203 | 2.5 | 32.5 | 57.5 | 7.5 | 3.9 | 6.0 | 90.0 | NF | NF | NF |
| 17 | 8 | 80 | 12 | 25 | 400 | 435 | 35 | 6.0 | 78.0 | 14.0 | 2.0 | 27.9 | 7.1 | 65.0 | NF | NF | NF |
| 18 | 4 | 40 | 56 | 25 | 400 | 429 | 29 | 3.0 | 39.0 | 57.0 | 1.0 | 4.7 | 7.1 | 88.2 | NF | NF | NF |

What is claimed is:

1. A process for hydroxylating aromatic compounds having at least one substitutable hydrogen atom, said process comprising contacting a gaseous mixture of nitrous oxide and said aromatic compound, the molar ratio of nitrous oxide to aromatic compound being less than 0.5, with a catalyst and subsequently separating unreacted aromatic compound while maintaining sufficient inert gas in admixture with the nitrous oxide and aromatic compound such that the mixtures of nitrous oxide, aromatic and inert gas are non-flammable throughout the process.

2. A process for making phenol, said process comprising contacting a gaseous mixture of nitrous oxide and benzene, the molar ratio of nitrous oxide to benzene being less than 0.5, with a catalyst in a reactor under conditions selected to oxidize the benzene to phenol and separating unreacted benzene downstream of the reactor, and providing sufficient inert gas in admixture with the nitrous oxide and benzene such that the mixtures of nitrous oxide, benzene and inert gas are non-flammable throughout the process.

3. The process of claim 2 wherein nitrous oxide constitutes at least 0.3 mole percent of the gaseous mixture in the reactor.

4. The process of claim 3 wherein the ratio of benzene to nitrous oxide is sufficiently high to provide at least 50 mole percent of obtainable selectivity to phenol.

5. The process of claim 3 wherein the nitrous oxide constitutes less than 5 mole percent of the gaseous mixture in the reactor.

6. The process of claim 3 wherein the nitrous oxide constitutes less than 3 mole percent of the gaseous mixture in the reactor.

7. The process of claim 3 wherein the proportions of nitrous oxide, benzene, and inert gas are selected such that the adiabatic temperature rise in the reactor is less than 150 degrees centigrade.

8. The process of claim 7 wherein the reactor is operated substantially adiabatically.

9. The process of claim 7 wherein the temperature rise is less than 90 degrees centigrade.

10. The process of claim 9 wherein the reactor is operated substantially adiabatically.

11. The process of claim 3 wherein the molar ratio of nitrous oxide to inert gas is not greater than 0.25.

* * * * *